US 6,622,856 B2

United States Patent
Gallo et al.

(10) Patent No.: US 6,622,856 B2
(45) Date of Patent: Sep. 23, 2003

(54) RELIEF KIT

(75) Inventors: Anthony B Gallo, Warren, NJ (US); John Harrold Redding, Freehold, NJ (US)

(73) Assignee: Johnson & Johnson Consumer Companies, Inc., Skillman, NJ (US)

( * ) Notice: Subject to any disclaimer, the term of this patent is extended or adjusted under 35 U.S.C. 154(b) by 89 days.

(21) Appl. No.: 09/841,991

(22) Filed: Apr. 25, 2001

(65) Prior Publication Data

US 2002/0157972 A1 Oct. 31, 2002

(51) Int. Cl.⁷ ............................................. B65D 69/00
(52) U.S. Cl. ........................ 206/232; 206/570; 206/538
(58) Field of Search ................................. 206/232, 223, 206/541, 581, 538, 539, 540, 570; 424/451

(56) References Cited

U.S. PATENT DOCUMENTS

| | | | |
|---|---|---|---|
| 611,136 A | * | 9/1898 | Mason .......................... 206/538 |
| 1,480,865 A | * | 1/1924 | Slade ........................... 206/570 |
| 4,288,006 A | * | 9/1981 | Clover, Jr. ................... 206/538 |
| 4,344,646 A | | 8/1982 | Michel |
| 5,009,894 A | * | 4/1991 | Hsiao ........................... 206/540 |
| 5,042,652 A | | 8/1991 | Grindrod |
| D320,695 S | | 10/1991 | Shim |
| D321,985 S | | 12/1991 | Ward |
| D324,608 S | | 3/1992 | Forbes |
| 5,119,940 A | | 6/1992 | Grindrod |
| 5,123,527 A | | 6/1992 | Hustad |
| D336,719 S | | 6/1993 | Newby, Sr. |
| D347,731 S | | 6/1994 | Hayakawa et al. |
| D351,504 S | | 10/1994 | Tarozzi |
| D353,265 S | | 12/1994 | Newby, Sr. |
| 5,379,887 A | * | 1/1995 | Conley, Jr. .................. 206/232 |
| D357,117 S | | 4/1995 | Huang |
| D369,240 S | | 4/1996 | Newby, Sr. |
| D370,557 S | | 6/1996 | Ferris et al. |
| D370,563 S | | 6/1996 | Sijmons |
| 5,529,205 A | | 6/1996 | Corney et al. |
| D384,501 S | | 10/1997 | Rosen |
| 5,709,308 A | | 1/1998 | Gics |
| D390,357 S | | 2/1998 | Rosen |
| 5,718,245 A | | 2/1998 | Horn |
| 5,743,402 A | | 4/1998 | Gics |
| D399,652 S | | 10/1998 | Fang |
| 5,848,700 A | * | 12/1998 | Horn ........................... 206/570 |
| 5,850,919 A | * | 12/1998 | Freed .......................... 206/538 |
| D406,192 S | | 3/1999 | Schurman |
| 5,900,263 A | | 5/1999 | Gics |
| 5,900,264 A | | 5/1999 | Gics |
| D412,397 S | | 8/1999 | Liu |
| 5,931,304 A | | 8/1999 | Hammond |
| D413,440 S | | 9/1999 | Schurman |
| D413,727 S | | 9/1999 | Sijmons |
| D418,677 S | | 1/2000 | Sijmons |
| 6,016,915 A | | 1/2000 | Almond |
| D426,705 S | | 6/2000 | Fang |
| 6,077,530 A | * | 6/2000 | Weinstein et al. ........... 424/451 |
| D428,699 S | | 8/2000 | Gibson et al. |
| 6,116,426 A | * | 9/2000 | Slonim ........................ 206/570 |

FOREIGN PATENT DOCUMENTS

| | | |
|---|---|---|
| CA | 76895 | 2/1995 |
| CA | 2165236 A1 | 6/1996 |

OTHER PUBLICATIONS

The Handbook of Package Engineering, J.F. Hanlon, 1984, ISBN 0–07–02594–1, pp. 8–44 to 8–80.

* cited by examiner

Primary Examiner—Luan K. Bui
(74) Attorney, Agent, or Firm—Michele G. Mangini

(57) ABSTRACT

A kit that is useful for relieving humans, and in particular infants, from discomfort is disclosed. Examples of such discomfort include fever, pain, congestion, skin irritation, and irritability. The kit includes an inner container having a plurality of compartments and at least one product for comforting humans packed in one of the compartments. Optionally, the inner container may be placed inside of an outer container.

4 Claims, 2 Drawing Sheets

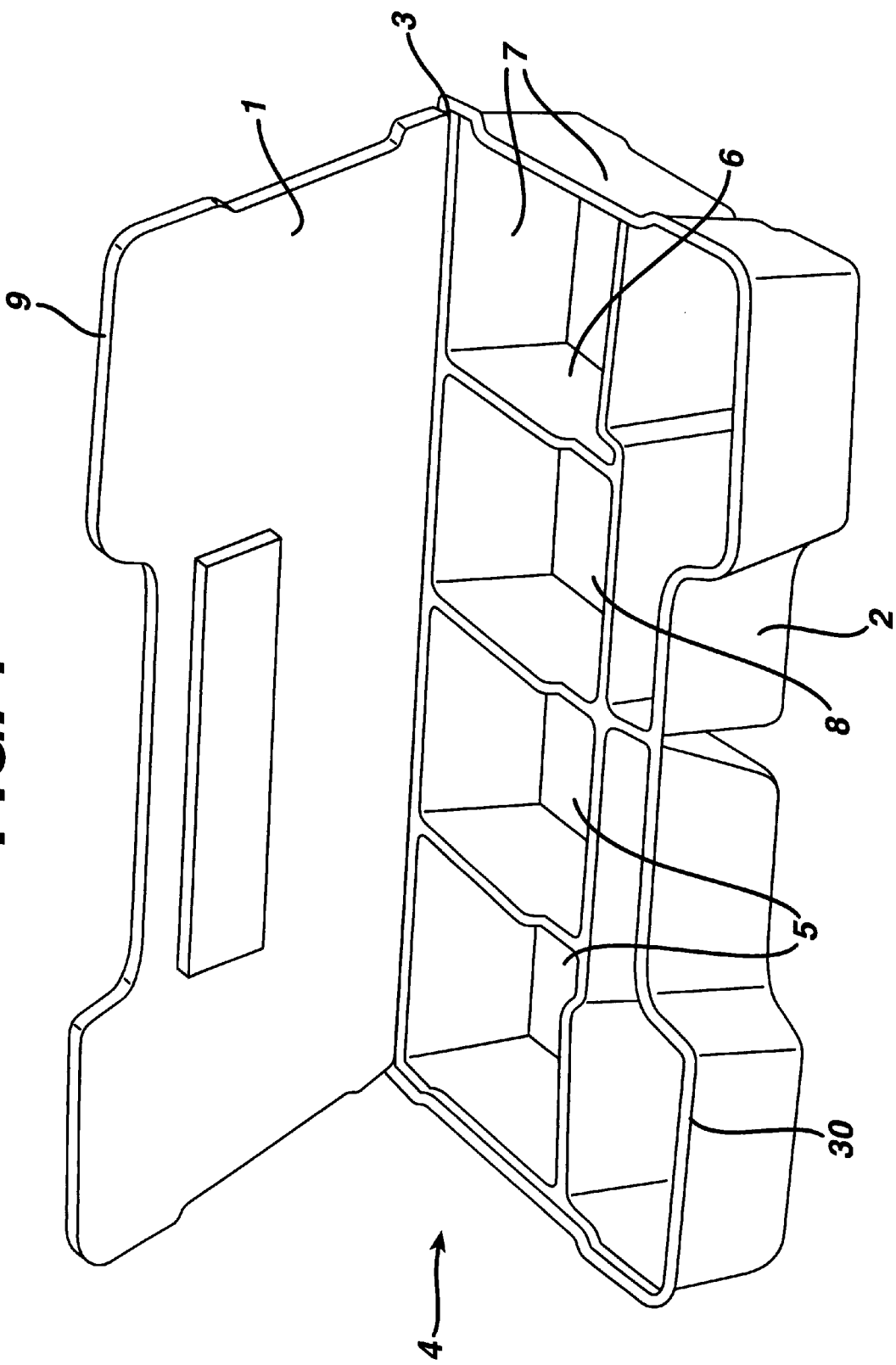

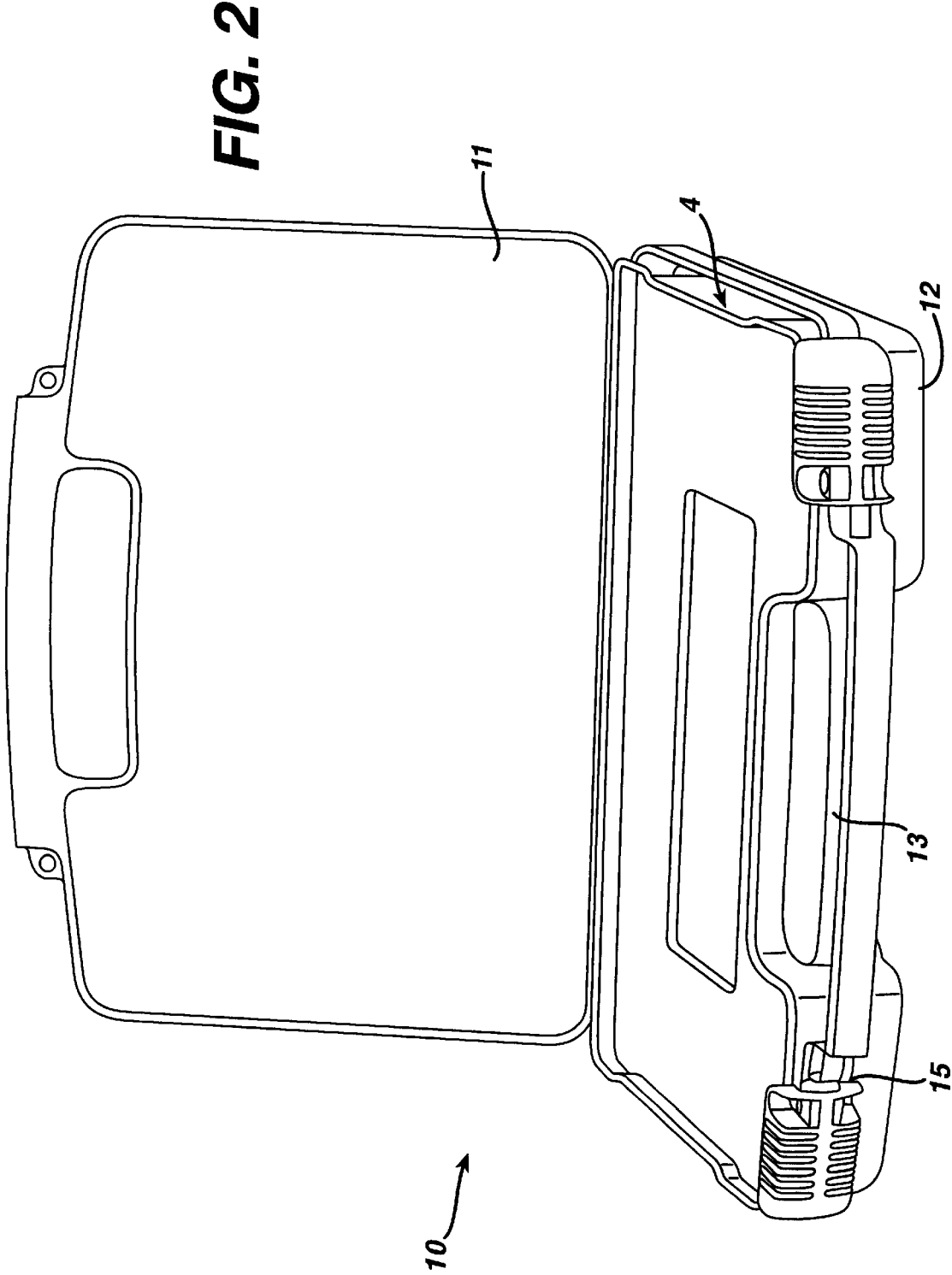

RELIEF KIT

BACKGROUND OF THE INVENTION

1. Field of the Invention

The present invention relates to a kit that is useful for relieving children from discomfort. Examples of such discomfort include, but are not limited to, fever, pain, congestion, gas, skin irritation, and irritability.

2. Description of the Prior Art

First time parents in particular are frequently overwhelmed at the number of products needed to care for and comfort a child. Not only do children have many different needs, but they also have many different potential causes for their discomfort. The method for treating each cause often necessitates the use of a different product.

For example, when a child catches a cold, it is common to purchase an acetaminophen or ibuprofen product and give it to the child in order to reduce the fever and pain associated with the cold. It is also common to purchase a cold medicine and give it to the baby to treat the sniffles, sneezes, congestion, and coughs associated with the cold. Many parents also purchase products that emit a congestion-relieving vapor. The latter are typically available in ointments to be applied to the child's chest, or in bath wash, which is placed in a bath, such that the child inhales the vapors.

Another problem faced in particular by babies is diaper rash, which can be quite uncomfortable. Parents typically purchase ointments and apply them to the irritated area of the baby in order to relieve the discomfort and heal the rash. Babies also frequently suffer discomfort due to gas pain. Parents frequently purchase products and give them to the baby to relieve gas pain.

As can be seen from the above discussion, parents may spend a lot of time running to the store for different products for relieving the discomforts of their children. Even after the parents have purchased all of the necessary treatment products for the child, the volume of products takes up a lot of space and is hard to organize. Quite often, a parent may have the appropriate product in the home but is unable to quickly locate and access the needed product.

U.S. Pat. No. 5,931,304 discloses a first aid kit that organizes first aid supplies, provides instructions for various first aid emergencies, and can be re-stocked with first aid supplies. However, to our knowledge, no such kit has been disclosed for the relief of problems that often cause children to be uncomfortable.

Therefore, there is a need for a kit that conveniently provides many of the products needed to relieve children from discomfort and which also organizes them in an effective manner. It may be further desired to provide instructions on how to recognize symptoms for certain problems as well as how to care for the particular problem that may be causing the child's discomfort. It would further be desirable to have a kit that would enable the user to replenish the products contained therein after a comfort situation is encountered without the need to buy a new kit.

SUMMARY OF THE INVENTION

We have discovered that it is possible to provide a kit that contains or may contain many of the products necessary to relieve the discomforts of children comprising: a.) an inner container having a multiplicity of compartments; and b.) at least one product for relieving a child from discomfort.

Advantageously, the kit can be re-stocked and is effective for conveniently organizing the products needed for comforting children, and infants in particular.

BRIEF DESCRIPTION OF THE DRAWINGS

The invention will be more fully understood and further advantages will become apparent when reference is made to the following detailed description of the invention and the accompanying drawings in which:

FIG. 1 is an isometric view of the inner container 4 shown in an opened position.

FIG. 2 is an isometric view of the inner container 4 located inside of the outer container 10, which is shown in an opened position.

DETAILED DESCRIPTION OF PREFERRED EMBODIMENTS

As used herein, the term "child" shall mean a person between the ages of about 0 to about 12 years old, and includes infants between the ages of 0 to about 3 years old.

As shown in FIG. 1, the present invention requires an inner container 4 having one or more compartments 5. Such inner containers 4 may be comprised of soft, flexible materials or from relatively more rigid materials such as plastics and cardboard. Examples of suitable soft, flexible materials include, but are not limited to, nylon, paper, flexible polyvinyl chloride, flexible polyolefin, and fabric such as cotton canvas. Examples of suitable plastics include, but are not limited to polyethylene, polypropylene, polycarbonate, polyvinyl chloride, polystyrene, polyethylene terephthalate, and mixtures and copolymers thereof.

In the embodiment wherein the inner container 4 is comprised of plastic, the inner container 4 may be molded to have a bottom 2 having a multiplicity of compartments 5, and an optional top 1. The top 1 and the bottom 2 may be separate and connected by any fastening means known in the art such as hinges, Velcro, snaps, zippers, hook and loop style fastener, stitches, couples, clamps, dowels, and the like. The hinges, which may be comprised of plastic, fabric, paper, and/or metal, may be held in place by any holding means known in the art, such as screws, tacks, rivets, adhesives, bolts, pins, and the like.

Alternatively, the inner container 4 may be arranged in a claim shell blister package configuration wherein the top 1 and bottom 2 are comprised of one piece of material, such as plastic, that is folded over onto itself. As shown in FIG. 1, a hinge 3 is formed in the portion of the container 4 between the top 1 and the bottom.

The inner container 4 may be designed such that when the top 1 is closed on top of the bottom 2, the rim 9 along the perimeter of the top 1 is inserted into the groove 30 along the perimeter of the bottom 2 to form a seal.

Although the thickness of the material selected to form the top 1 and the bottom 2 may vary based upon, for example, the type of material selected and the weight of the container's contents, in embodiments wherein the material is plastic, the thickness of the material may range from about 0.010 in to about 0.040 in, for example from about 0.020 in to about 0.030 in.

The compartments 5 may be formed by securing dividers 6 to the side walls 7 and/or the floor 8 of the bottom 2 of the inner container 4. The dividers 6 may be comprised of any material suitable for use as the inner container 4. In each embodiment, the dividers 6 and the inner container 4 may be comprised of either the same or different type of material.

The dividers 6, which may either be removably connected to or integral with the sidewall 7 and/or the floor 8, may be held in place by any of the above-mentioned fastening means or holding means. For example, in embodiments wherein the inner container 4 is comprised of cloth, the dividers 6 may be sewn in place. Alternatively, dividers 6 may be comprised of plastic or cardboard and inserted in or molded into the inner container 4 to form compartments 5.

Although the number of compartments 5 may vary, depending on, for example, the number of products to be contained and the size of the container 4, typically, the container has from about 3 to about 10, for example from about 4 to about 8 compartments 5.

The size and shape of each compartment 5 may vary, depending on, for example, the type and size of products to be contained therein and the size of the container 4. For each product in the container 5, it is preferable to include at least one compartment of sufficient dimensions to not only hold the product, but also to retain the product in place while carrying the container. For example, if a box of cold medicine having dimensions of 6 cm in length, 3.5 cm in depth, and 10.5 cm in height is to be included in the container, the size of the compartment will range in length from 6.5 cm to 9 cm, depth from 4 cm to 6 cm, and height from 11 cm to 13 cm. In general, the size of the compartments will be slightly larger in all dimensions than the products to be contained therein. The shape of the compartment 5 preferably approximates that of the product to be contained therein. For example, a rectangular box is preferably secured in an approximately rectangular-shaped compartment.

In one embodiment, the inner container 4 may be provided with one or more ancillary compartments for purposes of storing items other than comforting products therein. This is particularly useful for parents who may want to tailor the contents of the kit to their specific needs. For example, the inner container 4 may be provided with 8 compartments and 6 products. The extra 2 compartments could then be utilized for storing products that meet the parent's specific needs such as, for example, brushes, diapers, wipes, diaper disposal bags, and the like.

Optionally, the inner container 4 may have a handle (not shown). The handle may be integral to the inner container 4, e.g. formed as part of the inner container in the molding process, or alternatively, may be made separately and secured to the inner container by any fastening or holding means known in the art, such as those set forth above.

As shown in FIG. 2, the inner container 4 may be inserted into an outer container 10. The configuration of the inner container 4 is such that it completely fits inside of the outer container 10 as shown in FIG. 2. The inner container 4 and the outer container 10 may be made from the same material or from different materials. The outer container 10 may be comprised of any of the materials set forth above for the inner container 4. In a preferred embodiment, the outer container 10 is more rugged than the inner container 4 in order to protect the contents of the container 4. As used herein, "rugged" is meant that the top 11 and the bottom 12 of the outer container 10 are either thicker and/or are comprised of a material having a greater hardness than the material used for the inner container 4 for purposes of improving the crush-resistance of the outer container 10. The rugged outer container therefore is relatively more durable than the material used for the inner container 4.

Although the thickness of the top 11 and the bottom 12 of the outer container 10 vary depending upon the size and amount of products contained therein and the type of material used, but typically may range from about 0.01 in to about 0.13 in, for example from about 0.3 in to about 0.9 in.

The top 11 and the bottom 12 of the outer container 10 may be comprised of separate pieces that are connected by any of the above-mentioned fastening means. In one embodiment, the top 11 may be snapped into the bottom 12 and secured by an integral hinge means. Alternatively the top 1 and bottom 2 may be comprised of one piece of plastic in a clam shell blister package configuration.

The outer container 10 may also have ancillary compartments (not shown) for holding other miscellaneous items such as diapers, wipes, pacifiers, cups, bottles, and the like. These ancillary compartments may be comprised of the same materials and have the same shapes as those described above for the compartments 5 in the inner container. The compartments may also be in the shape of a pocket or folder, which would be especially suitable for holding medical information describing, for example, a child's symptoms and possible products to provide relief therefrom, a conversion chart for determining the amount of medicine to give to the baby, or cardio-pulmonary resuscitation instructions. The kit may contain a first aid booklet may be included in the kit. However, the kit is not a substitute for treatment by a physician. It is intended that the products in the kit can be utilized by parents when they know the cause of the problem and can not get the child to the doctor right away, or when the child has been seen by the doctor, and the products are appropriate for relieving the symptoms of the problem that the child may have.

Optionally, the outer container 10 may have a handle 13. The handle 13 may be integral to the outer container 10, e.g. formed as part of the outer container in the molding process, or alternatively, may be made separately and secured to the outer container by any fastening or holding means known in the art, such as those set forth above. In addition to, or in place of the handle 13, the outer container 10 may have a shoulder strap or string (not shown). The strap or string may be made of any flexible material known in the art such as, for example, yarn, leather, flexible plastic strip, cloth, and the like, and may be attached to any location on the outer container 10 by any fastening or holding means known in the art, such as those set forth above.

The outer container 10 may also be provided with one or more locking means 15 for purposes of keeping the top 11 and bottom 12 closed when the kit is not in use. Such locking means 15 are known in the art, and include, but are not limited to, slideable locks, snap locks, clip locks, and hooks and loops. In an alternative embodiment, the locking means 15 may employ any of the known child resistant features known in the art.

The shape of the outer container 10 is not critical and thus may resemble, for example, a purse, a briefcase, back-pack, or a traditional diaper bag.

In embodiments wherein a plastic inner container 4 or outer container 10 is used, such containers may be manufactured via any molding means such as, for example, thermoforming, extrusion, or injection molding processes. Details of such processing are well known in the art and disclosed in, for example, Hanlon, J., The Handbook of Package Engineering, ISBN 0-07-02594-1, which is incorporated by reference herein.

The kit further contains at least one product for relieving babies from discomfort. Suitable products include, but are not limited to, those that provide pain relief and/or fever reduction, such as, but not limited to acetaminophen and ibuprofen; products that remove bacteria from the skin such as those containing Triclosan and/or benzalkonium chloride; products that provide relief for diaper rash, such as, but not limited to those containing zinc oxide; products for providing itch relief, such as, but not limited to those containing diphenhydramine or calamine; products designed to be ingested for the relief of the symptoms of the common cold, such as, but not limited to those containing at least one cough suppressant such as dextromethorphan and/or a decongestant such as pseudoephedrine; products that provide relief for gas pain, such as, but not limited to those containing simethicone; products that provide local anesthesia, such as, but not limited to those containing benzocaine, for example teething gels; products that provide congestion-relieving vapors for inhalation such as, but not limited to bath washes or rub on ointments containing, for example, eucalyptus, menthol, and the like, or fragrances known in the art; and products that help soothe babies such as baths, powders, lotions and the like containing for example, chamomile and lavender.

The kit may also contain other ancillary products including, but not limited to antibiotic ointments, such as Neosporin and the like; lubricants such as petroleum jelly; saline drops; powder; syrup of Ipecac; bandages; nail clippers; anti-inflammatory creams, such as those containing cortisone; thermometer strips; cotton balls; rubbing alcohol; cotton swabs; sunscreen; insect repellant; baby oil; instant ice packs; hydrogen peroxide; lotions containing Aloe Vera for soothing sunburn; and solutions for replacing lost electrolytes, such as Pedialyte®.

The kit preferably contains a multiplicity of products for relieving children from discomfort. For example, the kit may contain at least one product for pain relief and/or fever reduction, at least one product for gas pain relief, and at least one product for relief of the symptoms of the common cold, e.g. decongestant and/or cough suppressant. In a preferred embodiment, the kit contains an acetaminophen product for fever reduction and pain relief; an ibuprofen product for fever reduction and pain relief; a cold medicine containing a decongestant and a cough suppressant; a product for the relief of gas pain; a product for the relief of diaper rash; a bulb syringe; and antibacterial towelettes.

The invention illustratively disclosed herein suitably may be practiced in the absence of any component, ingredient, or step which is not specifically disclosed herein. An example is set forth below to further illustrate the nature of the invention and the manner of carrying it out. However, the invention should not be considered as being limited to the details thereof.

EXAMPLE

A hinged clam shell inner container was formed by thermoforming polyethylene terephthalate at a temperature of about 240° F. to about 260° F. in the shape of the inner container set forth in FIG. 1. The inner container had a top, a bottom, and an integral hinge between the top and the bottom. The top and bottom were designed such that when the top was pressed against the bottom on the perimeter of the container, a seal was formed. The thickness of the top and bottom was 0.020 in. The length of the container was approximately 35 cm. The depth of the container was approximately 5.5 cm. The height of the container was approximately 23 cm. The bottom of the container possessed a total of 6 compartments, 4 of which were side by side and below 2 other compartments, the latter of which were also side by side. Two of the bottom compartments had lengths of 8 cm, depths of 5 cm, and heights of 12 cm. The other two bottom compartments had lengths of 7.5 cm, depths of 5 cm, and heights of 12 cm. The top compartments had lengths of 16 cm, depths of 5 cm, and flared heights of 5 cm to 7.5 cm.

The outer container illustrated in FIG. 2 was formed by injection molding polypropylene having a thickness of 0.030 in to 0.080 in at a temperature of about 400° F. to about 550° F. The resulting outer container was formed with an integral handle. The outer container was provided with 2 slidable locks located on both sides of the handle and at the point where the top of the outer container meets the bottom of the outer container. The dimensions of the container were 34.5 cm length, 8.5 cm depth, and 24.5 cm height (including the handle).

The following products were then added to the inner container: 0.5 ounce MOTRIN® Drops, 0.5 ounce Infants' TYLENOL® Cold, 0.25 ounce Infants' TYLENOL® Drops, 0.5 ounce Infants' MYLICON® Drops, 2 ounce JOHNSON'S® Diaper Rash Cream, 6 JOHNSON'S® antibacterial towelettes, 9 ounces JOHNSON'S® Soothing Vapor Bath, and a nasal aspirator. The products are suitable for use in accordance with their instructions apparent on their respective packages.

MOTRIN and TYLENOL are registered trademarks of McNeil Consumer Healthcare, a division of McNeil-PPC, INC., Fort Washington, Pa. MYLICON is a registered trademark of Johnson & Johnson•MERCK Consumer Pharmaceuticals CO., Fort Washington, Pa. JOHNSON'S is a registered trademark of Johnson & Johnson Consumer Companies, Inc., Skillman, N.J.

The inner container was then inserted into the outer container to form an easy-to-carry kit that conveniently contained many products for relieving children from discomfort in an organized manner.

We claim:

1. A kit for comforting humans comprising:
 a. a plurality of products for comforting humans including:
  1) a pain relief and fever reduction product;
  2) an orally-administered nasal decongestant and couch suppressant product; and
  3) a gas relief product;
  4) a diaper rash relief; and
 b. an inner container having a multiplicity of compartments, wherein each compartment contains only one of said products, wherein the kit is easily carryable.

2. A kit for comforting humans comprising:
 a. a plurality of products for comforting humans including:
  1) a pain relief and fever reduction product;
  2) an orally-administered nasal decongestant and cough suppressant product; and
  3) a gas relief product;
  4) a diaper rash relief product; and
 b. an inner container having a multiplicity of compartments, wherein each compartment contains only one of said products, wherein the kit is easily carryable, and wherein the diaper rash relief product contains zinc oxide.

3. A kit for comforting humans comprising:
 a. a plurality of products for comforting humans including:
  1) a pain relief and fever reduction product containing acetaminophen or ibuprofen;
  2) an orally-administered nasal decongestant and cough suppressant product containing pseudoephedrine and dextromethorophan; and 3) a gas relief product containing simethicone; and
4) a diaper rash relief product; and b. an inner container having a multiplicity of compartments, wherein each compartment contains only one of said products and the kit is easily carryable.

4. The kit of claim 3 further comprising an outer container, wherein the inner container may be positioned completely inside of the outer container.

* * * * *